United States Patent [19]

Bryan

[11] Patent Number: 5,498,262

[45] Date of Patent: Mar. 12, 1996

[54] SPINAL FIXATION APPARATUS AND METHOD

[76] Inventor: Donald W. Bryan, 6151 S. Woodland Dr., Ogden, Utah 84403

[21] Appl. No.: 232,371

[22] Filed: Apr. 25, 1994

Related U.S. Application Data

[63] Continuation-in-part of Ser. No. 999,005, Dec. 31, 1992, Pat. No. 5,306,275.

[51] Int. Cl.$^6$ .................................................. A61B 17/00
[52] U.S. Cl. .................................. 606/61; 606/53; 606/72
[58] Field of Search ............................... 606/53, 60, 61, 606/66, 72, 73

[56] References Cited

U.S. PATENT DOCUMENTS

| | | | |
|---|---|---|---|
| 4,920,959 | 5/1990 | Witzel et al. | 606/53 |
| 5,122,131 | 6/1992 | Tsou | 606/61 |
| 5,171,279 | 12/1992 | Mathews | 606/61 |
| 5,219,349 | 6/1993 | Krag | 606/53 |
| 5,242,445 | 9/1993 | Ashman | 606/61 |
| 5,261,907 | 11/1993 | Vignaud et al. | 606/60 |
| 5,352,225 | 10/1994 | Yuan et al. | 606/61 |
| 5,360,429 | 1/1994 | Jeanson et al. | 606/61 |
| 5,380,325 | 1/1995 | Lahille et al. | 606/61 |

FOREIGN PATENT DOCUMENTS

| 553424 | 8/1993 | European Pat. Off. | 606/61 |
|---|---|---|---|

*Primary Examiner*—Stephen C. Pellegrino
*Assistant Examiner*—Jeffrey A. Schmidt
*Attorney, Agent, or Firm*—J. Winslow Young

[57] ABSTRACT

An implantable spine fixation apparatus and method, the apparatus including a pair of longitudinal rods placed on each side of the spinous process. Several side arm clamps are attached to the longitudinal rods with their lateral arms extending outwardly from the longitudinal rods. Clamps are mounted to the lateral arms and both affixed to the bone of the spine and clamped to the lateral arms by bone screws inserted into the bone of the spine. Cross link plates are mounted to paired side arm clamps to secure the relative positions of the longitudinal rods. The method includes providing the bone screw with the optimal angular orientation for fixation of the bone screw to the bone. The method also includes adjustably affixing the implantable fixation apparatus relative to the spine for improving bone grafting.

19 Claims, 4 Drawing Sheets

SPINAL FIXATION APPARATUS AND METHOD

RELATED APPLICATIONS

This patent application is a continuation-in-part application of my application Ser. No. 07/999,005 filed 31 Dec. 1992 for LUMBAR SPINE FIXATION APPARATUS AND METHOD (now U.S. Pat. No. 5,306,275 issued 26 Apr. 1994).

BACKGROUND

1. Field of the Invention

This invention relates to instrumentation for achieving spinal fusion and, more particularly, to an interchangeable component system and method for fixation of the lumbar spine and the lumbosacral spine to aid the fusion of these regions of the spine.

2. The Prior Art

The spine is a flexible, multisegmented column that supports the upright posture in a human while providing mobility to the axial skeleton. The lumbar spine serves two basic functions. It encases and protects vital neural elements and provides structural support for the body by transmitting the weight of the body through the pelvis to the lower extremities. Since there are no ribs attached to it, the lumbar spine has a relatively wide range of motion.

The spine is made up of bone, intervertebral discs, synovial joints with their articular cartilage, synovial capsules and, as part of the back, is surrounded by supporting ligaments, muscle, fascia, blood vessels, nerves, and skin. As in other areas of the body, these elements are subject to a variety of pathological disturbances: inflammation, trauma, neoplasm, congenital anomalies, etc. In fulfilling its role in the back, the spine can be subjected to significant trauma which is assumed to play a dominant role in the etiology of low back pain. Trauma frequently results in damage at the upper end of the lumbar spine, where the mobile lumbar segments join the less mobile dorsal spine. Excessive forces on the spine can not only produce life-threatening traumatic injuries but may contribute to an increased rate of degenerative change. Degenerative changes tend to develop in the lower lumbar intervertebral discs, most commonly in the third decade. Osteoarthritis produces changes in the facet joints by middle age. Pain in the low back is a complaint of about 80% of the members of the human race at some period of life and is responsible for a large percentage of patient visits to physicians.

One of the methods used to treat disabling pain and neurological compromise produced by any of the above noted pathological conditions has been spinal fusion. Spinal fusion has been a controversial topic since the first procedures were performed in the early 1900's. Indications and techniques were argued then and continue to be a constant source of lively discussion in the orthopedic literature. It is also interesting to note that the development of spinal fusion techniques predates the understanding and surgical treatment of lumbar disc disease. It is the intersection and intermingling of indications for these two procedures, disc excision and lumbosacral fusion, that have produced the most controversy.

The earliest spinal fusion techniques were basically posterior interlaminar fusions. Subsequently, a few years of experience with these techniques led to the evolution of posterolateral techniques allowing a larger area for bone grafting and fusion. However, as orthopedists recognized the relatively high rate of unsatisfactory results with the traditional fusion techniques, they developed new techniques. The continued evolution of lumbosacral fusion has involved the use of hardware or instrumentation in an attempt to achieve either stability and thus fusion or correction of deformity and stability followed by fusion. When one considers the numbers of patients who have been treated surgically and followed for decades, it is amazing that it is still not possible to garner a strong scientific consensus on the efficacy of lumbosacral fusion from the literature. Various studies have been conducted over the past several decades and have determined that satisfactory results were obtained in 60% of the cases with disc excision alone and 70% satisfactory results in the fusion group. The conclusion was that despite the slightly better results in the fusion group, the morbidity risk from the fusion procedure meant that the indicated operation was disc excision alone with the recommendation that fusion be performed later if the patient failed with persistent symptoms secondary to instability or degenerative changes. Another study that looked into all aspects of instability whether in the vertical plane (narrowing, olisthesis), the horizontal plane (articular process disease), the frontal plane (scoliosis), and the sagittal plane (spondylolisthesis, compression fracture) concluded that only about one-third of these patients should be fused primarily. However, based upon my experience as an orthopedic surgeon, I have concluded that the ambiguous results from the earlier studies were the result of inadequate, cumbersome, and poorly designed instrumentation for achieving fixation in aid of lumbar fusion.

One can well ask, why use instrumentation in lumbosacral fusion. Fusion is performed in the unstable spinal segment that one wants immobile. Internal fixation increases rigidity and results in a high rate of fusion. This increased fusion rate and decreased pseudarthrosis rate give better results and can significantly reduce postoperative pain and time for convalescence. Spinal instrumentation also allows correction of deformities and maintenance of that correction during consolidation by fusion. Although there are no generally accepted answers to the question of what are the general indications for instrumentation, it is possible to propose a logical schema to guide the spinal surgeon in making these important decisions. The primary considerations are the magnitude of instability, the plane of deformity, and the available intact anatomy.

The past decade or two has seen an extensive development of internal fixation devices for the lumbar and lumbosacral spine. The most common rationale for using such devices is to reduce the incidence of pseudarthrosis after bone grafting. Another rationale (typically for trauma management) is to maintain intervertebral alignment to protect the neural elements until healing occurs. One of the early fixation methods involved the placement of screws obliquely across each facet joint involved in the grafting. However, the pseudarthrosis rate for this procedure was unacceptably high. Numerous other types of devices that variously include plates, wires, rods, bolts, hooks, and, of course screws, have evolved since that time and have resulted in a plethora of devices being available for use by the orthopedic surgeon. Although not provided by all these devices, the ideal device would provide internal alignment and fixation not just in any one of the various planes of movement but in a full, three-dimensional construct.

Numerous patents have been issued for various types of spine fixation devices. These devices employ different mechanical apparatus for enabling the surgeon to selectively adjust the alignment of the patient's spine and then to secure that alignment with the spine fixation device. Edwards (U.S. Pat. No. 4,569,338) discloses a sacral fixation screw having an opening through the head of the screw. A rod-mounted hook is mountable to the opening to interconnect the rod to the sacrum for spinal fixation purposes.

Steffee (U.S. Pat. Nos. 4,648,388 and 4,719,905 discloses a rod, a plurality of clamps, and a plurality of fastener assemblies. The clamps are fastened to selected vertebra and the clamps are tightened against the rod which has been selectively bent to conform to a preselected contour to hold the spine in the desired orientation.

Howland et al (U.S. Pat. No. 4,653,481) disclose a plurality of screw clamp assemblies that are inserted into the vertebral body through the pedicle and are used as anchors for rigid rods which have been selectively bent to conform to a preselected contour to hold the spine in the desired orientation.

Puno et al (U.S. Pat. No. 4,805,602) disclose a transpedicular screw and rod system for the internal fixation of the spine. The rod is held in position against the vertebral lamina by an anchor which is secured to the vertebrae by the transpedicular screw.

Heinig et al (U.S. Pat. No. 4,887,595) disclose a surgically implanted device for correcting and maintaining the relative relationship of the spinal bodies of a spinal column. The apparatus includes a plate portion and a rod extending from the plate portion.

Sherman (U.S. Pat. No. 4,887,596) discloses an open backed pedicle screw for use in internal spinal fixation. The open back includes a yoke for receiving a rod and a clamping mechanism for clamping the rod against a cusp in the yoke while permitting angular adjustment between the rod and the yoke.

Witzel et al (U.S. Pat. No. 4,920,959) disclose an external fixture for bone synthesis.

Gotzen et al (U.S. Pat. No. 4,944,743) disclose an implantable fixation device having a support bar having right-hand threads on one end and left-hand threads on the other end. Jaw supports are threadedly mounted on the respective threaded ends. Bolt jaws are secured to the jaw supports and affixed to intact vertebral bodies of the spinal column.

Gaines, Jr. (U.S. Pat. No. 4,950,269) discloses a spinal column fixation device for connecting vertebrae. The device includes a pedicle screw and a mounting system for mounting a rod to the head of the screw. A cap is engageable on the screw head and is used to retain the rod to the screw.

Krag et al (U.S. Pat. No. 4,987,892) disclose a spinal fixation device wherein at least two pedicle screws are interconnected by a rod. Clamps adjustably secure the rod to the pedicle screws.

Cotrel (U.S. Pat. No. 5,005,562) discloses a spinal fixation device including pedicle screws, and sublaminar hooks interconnected by rods. The pedicle screws and the sublaminar hooks are configured with an open, threaded yoke into which a set screw is threadedly inserted to secure the rod to the pedicle screw and the sublaminar hook.

Howland (U.S. Pat. No. 5,030,220) discloses a spine fixation system including pedicle screws, saddle assemblies, and rods which are securely engaged by the saddle assemblies.

Tsou (U.S. Pat. No. 5,122,131) discloses a device for secure mechanical coupling to an elongated surgical rod.

Ashman (U.S. Pat. No. 5,242,445) discloses a device very similar to that of Tsou Cotrel (U.S. Pat. No. 5,154,719) discloses an implant for an osteosynthesis device including a body for fixation on a rod.

Schläpfer (U.S. Pat. No. 5,190,543) discloses a pedicle screw with a slotted head for receiving a support rod. Limited pivotal movement for the support rod is provided by a transverse support element in the head.

Mehdian (U.S. Pat. No. 5,217,497) discloses an implant of a nature similar to that of Cotrel for fixing a rod to a pedicle screw.

Krag et al (U.S. Pat. No. 5,219,349) a spinal fixator reduction frame for securement to shaft handles extending from the pedicle screws of a Vermont Spinal Fixator type implant.

However, my experience has shown that each of these prior art devices are either cumbersome to implant, difficult to adjust, or require undue surgical time in their implantation. Further, since there is such a wide variation in spinal dimensions and availability of suitable attachment sites, certain of these devices have only limited application. Another problem equally important is that of accurate placement of the pedicle screws followed by subsequent adjustment of the interconnecting rods, wires, hooks, etc., once the pedicle screws are in place.

In view of the foregoing, it would be a significant advancement in the art to provide a spinal fixation apparatus and method that is highly adaptable in its placement, easily adjustable after securement of the pedicle and/or sacral screws, and provides ample support or fixation in all planes. It would also be an advancement in the art to provide a spinal fixation apparatus and method wherein the pedicle screws are quickly and accurately placed for providing the optimal securement of the screws. Such a novel spinal fixation apparatus and method is disclosed and claimed herein.

BRIEF SUMMARY AND OBJECTS OF THE INVENTION

This invention is a novel spinal fixation apparatus and method and includes specially designed clamps, side arm clamps, and cross link plates all of which interconnect with longitudinal rods and are used for spinal fixation in combination with bone screws. The various components can be selectively interlocked in an almost infinite number of orientations to provide the inventive spinal fixation apparatus of this invention with an almost infinite variability in placement and subsequent securement, limited only, of course, by the relatively fixed number of attachment points for the novel spinal fixation apparatus of this invention.

It is, therefore, a primary object of this invention to provide improvements in spinal fixation apparatus.

Another object of this invention is to provide improvements in the method for fixation of a spine for fusion.

Another object of this invention is to provide a cross link plate for interconnecting a pair of lumbosacral rods.

Another object of this invention is to provide an interlock for interlocking the cross link plates to the longitudinal rods and to bone screws embedded in the bone of the spine.

Another object of this invention is to provide a side arm clamp for use in anchoring the longitudinal rod to the pedicle of the vertebrae.

Another object of this invention is to provide a lateral clamp for anchoring to a longitudinal rod, the lateral clamp having a side arm to which a pedicle screw may be clamped.

Another object of this invention is to provide a side arm clamp for attachment to the longitudinal rod and in engagement with the pedicle screw clamp.

These and other objects and features of the present invention will become more readily apparent from the following description in which preferred and other embodiments of the invention have been set forth in conjunction with the accompanying drawing and appended claims.

DETAILED DESCRIPTION OF THE PREFERRED EMBODIMENT

Figure 1:
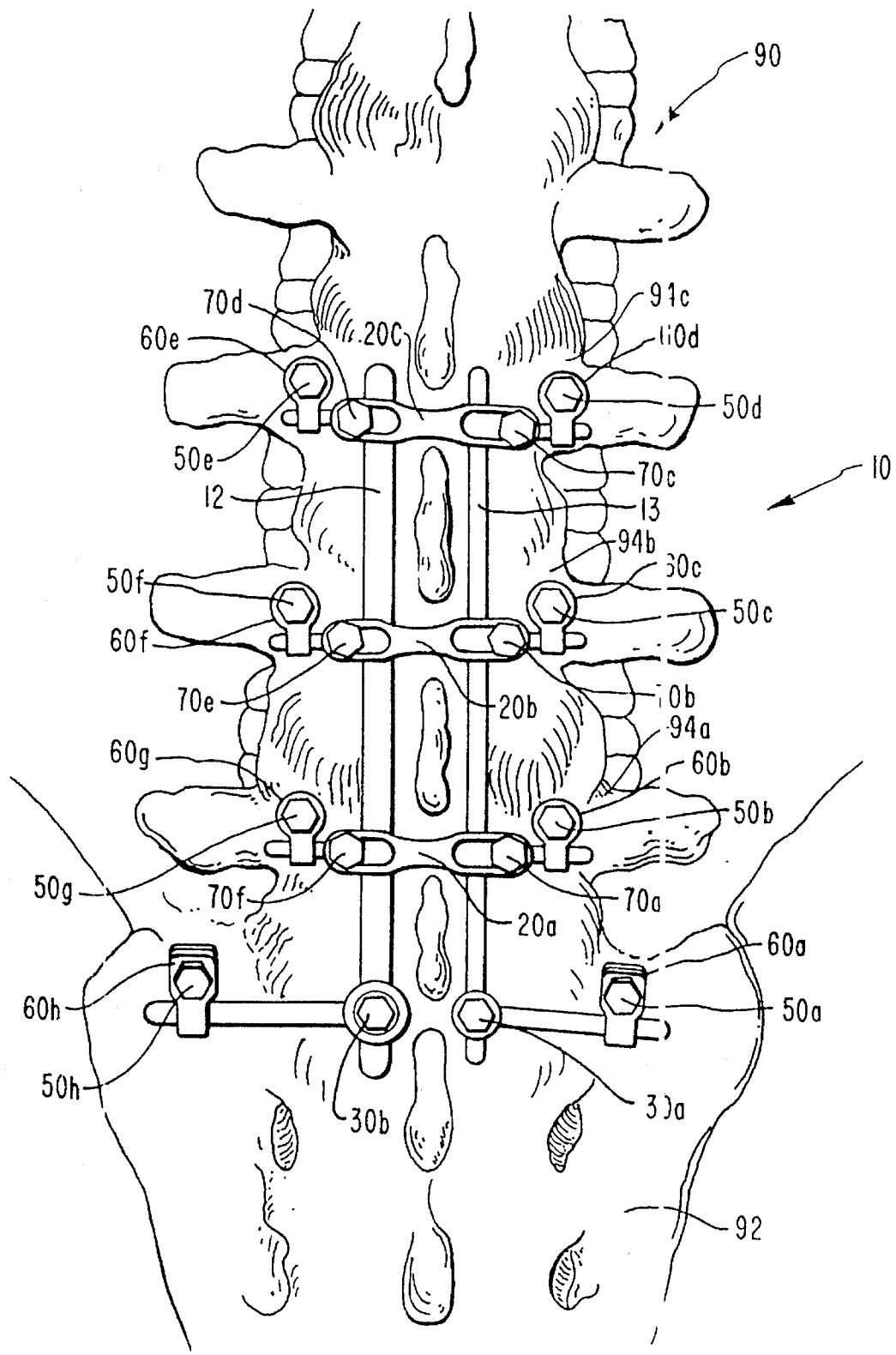
FIG. 1 is a plan view of the spine fixation apparatus of this invention shown in the environment of a portion of the lumbosacral spine.

The invention is best understood from the following description with reference to the drawing wherein like parts are designated by like numerals throughout and taken in conjunction with the claims.

General Discussion

The underlying rationale for spinal fusion is to (a) restore the integrity of the spine or to replace missing bone stock, i.e., fracture, tumor, infection; (b) produce an arthrodesis that will suppress undesired movement between two or more bony elements that are the source of pain; and (c) maintain correction of spinal deformity or to prevent progression of deformity. In general, this arthrodesis is produced by using a bone graft that will heal and mature, binding the involved elements intimately. Arthrodesis requires in most instances a period of immobilization to achieve this end. Importantly, the key factor in predicting successful fusion is the amount of instability; that is, if instability is moderate and bone stock good, the proportion of easy primary fusion will increase. This goal is readily accomplished using the novel apparatus and method of this invention.

Since fusion is performed in the unstable spinal segment that one wants immobile, the use of the internal fixation apparatus increases rigidity and gives a higher rate of fusion. This resultant increased fusion rate and decreased pseudarthrosis rate gives better results and can ease postoperative management regimens. Therefore, spinal instrumentation allows correction of deformity and rigid fixation of that correction during consolidation by fusion.

The novel spinal fixation apparatus and method of this invention enables the surgeon to securely immobilize the desired number of lumbar vertebrae thereby providing a stable condition for the ingrowth of bone tissue to achieve true spinal fixation. Importantly, the spinal fixation components of this invention are configured to reduce, if not eliminate, the incremental movement or micromotion between the various components. The angular orientation of the bone screw placement is are designed to achieve optimal fixation between the device and the vertebrae to which it is affixed. The bone screws are specifically designed to anchor securely through the pedicle into the vertebral body and simultaneously secure a clamp to engage the side arm portion of either of two embodiments of a side arm clamp in a tight, non-release fashion.

I have also devised my lumbar spinal fixation apparatus with a high degree of adaptability so that it is a simple matter for the surgeon to adapt the various components of my system to meet the support requirements of almost any spinal condition encountered. My clamp and bone screw system also allows the surgeon to place supportive rods at almost any location along the length of the spinal column being treated.

Referring now to FIG. 1, the unique spinal fixation apparatus of this invention is shown generally as construct 10 mounted to the lumbar region of a spine 90. Spine 90 includes a sacrum 92 and a plurality of vertebra 94a–94d. Vertebra 94a–94d each include an upwardly extending spinous process along with a transverse process extending outwardly on each side, none of which are numbered herein for sake of simplicity in presenting this invention. A pair of longitudinal rods 12 and 13 are aligned on each side of spine 90. Longitudinal rods 12 and 13 are shown herein as constituting two different sizes of rods for the purpose of illustrating a unique feature of this invention in that construct 10 can utilize different sizes of components as predetermined by the surgeon (not shown). However, it is most likely that longitudinal rods 12 and 13 will be selected from the same diameter in the assembly of construct 10. Longitudinal rods 12 and 13 are mounted on each side of the spinous process and provide the longitudinal support for spine 90.

Construct 10 is assembled from two types of lateral clamps, side arm clamps 30a, 30b and 70a–70f, in combination with cross-link plates 20a–20c, clamps 60a–60h, and bone screws 50a–50h, all of which will be discussed more fully hereinafter. Side arm clamps 30a and 30b are each affixed to the lower ends of longitudinal rods 13 and 12, respectively. Clamps 60a and 60h provide the mechanism for enabling bone screws 50a and 50h to secure these elements to sacrum 92. Correspondingly, side arm clamps 70a–70f in combination with clamps 60b–60g and bone screws 50b–50g, respectively, provide the necessary securement of longitudinal rods 12 and 13 to vertebra 94a–94c, respectively. Cross-link plates 20a–20c provide the necessary bridging mechanism between longitudinal rods 12 and 13 by being clamped thereto by side arm clamps 70a–70f, respectively, when side arm clamps 70a–70f are secured to longitudinal rods 12 and 13, respectively.

Figure 2:
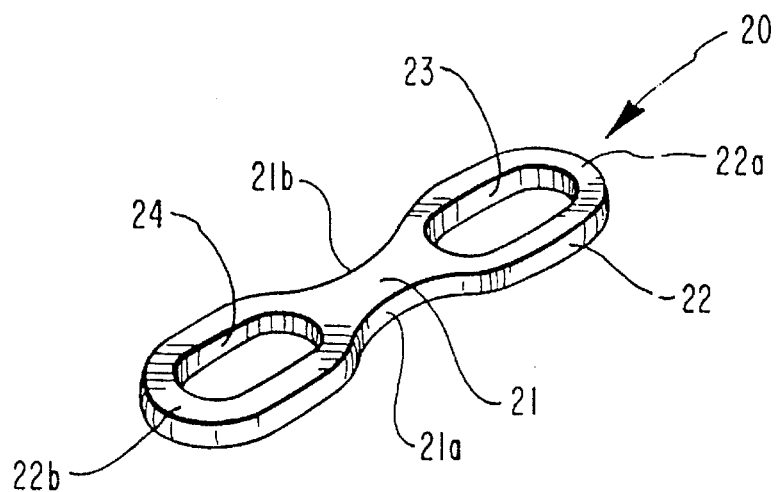
FIG. 2 is a perspective view of a cross link plate.

Referring now to FIG. 2, cross-link plate 20 is shown more clearly and includes a body 22 having a first end 22a and a second end 22b joined together by a strut 21. Strut 21 includes a waist-like configuration having a recess 21a on one side and a corresponding recess 21b on the other side. First end 22a includes an elongated slot 23 while second end 22b includes an elongated slot 24. Elongation of slots 23 and 24 provides the surgeon (not shown) with a limited degree of adjustability in securing cross-link plate 20 between longitudinal rods 12 and 13 (FIG. 1). Cross-link plate 20 is preferentially formed with at least one of recesses 21a and/or 21b to accommodate cross-link plate 20 being placed in close proximity to the adjacent spinous process of vertebra 94a–94c (FIG. 1). Further, the waist-like configuration formed by recesses 21a and 21b allows the surgeon to deformably shape cross-link plate 20 to create an upwardly convex curvature to cross-link plate 20 relative to spine 90 to thereby more accurately conform the spinal fixation apparatus of construct 10 to spine 90. Importantly, the ability to deformably shape cross-link plate 20 to spine 90 enables the surgeon to adjustably mount longitudinal rods 12 and 13 more accurately to spine 90. The elongation of slots 23 and 24 also provides limited lateral adjustability in mounting cross-link plate 20 to longitudinal rods 12 and 13.

Figure 3:
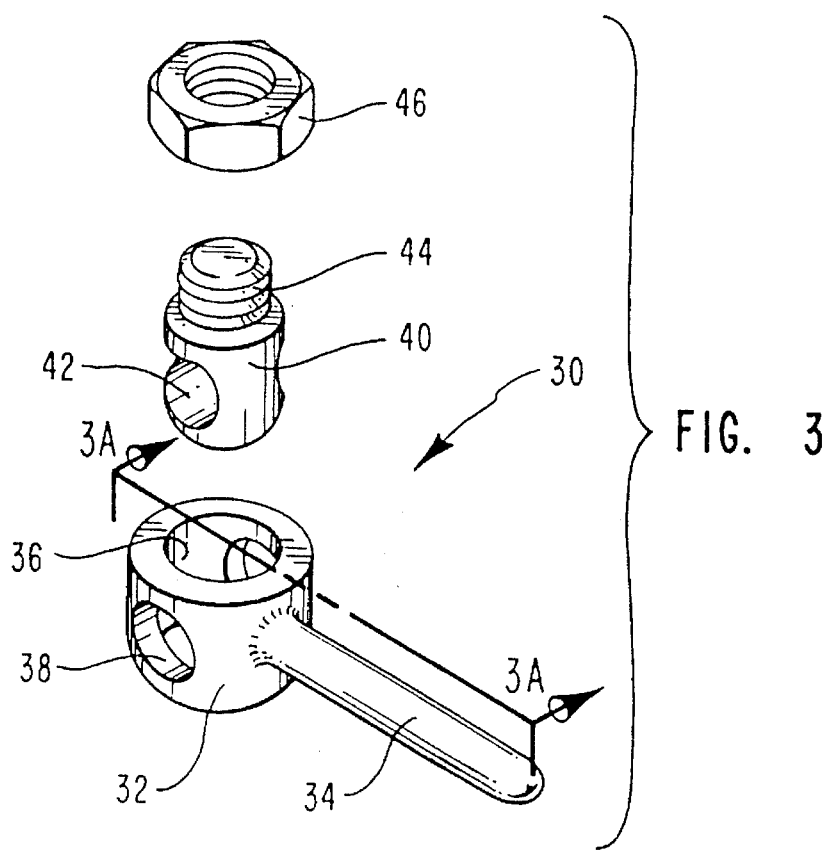
FIG. 3 is an exploded perspective view of a first side arm clamp.
Figure 3A:
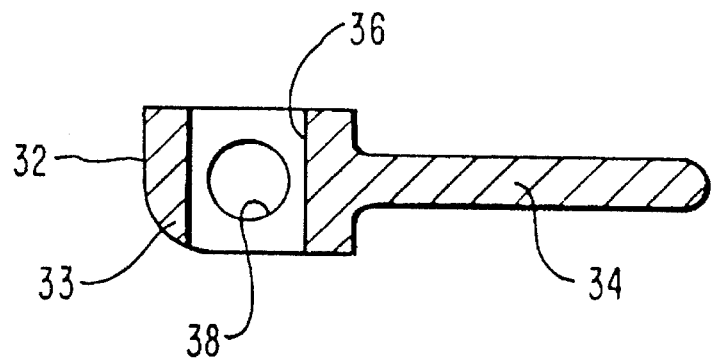
FIG. 3A is a cross sectional view taken along lines 3A—3A of FIG. 3.

Referring now to FIGS. 3 and 3A, a first preferred embodiment of the novel side arm clamp of this invention is shown generally at 30 and includes a clamp body 32 having a side arm 34 extending perpendicularly therefrom. Clamp body 32 is configured as a hollow cylindrical member having a hollow throughbore 36 formed axially therethrough. A transverse bore 38 is formed through body 32 orthogonal to the axis of side arm 34 and provides an anvil against which longitudinal rods 12 and 13 (FIG. 1) are clamped as will now be discussed. In particular, first side arm clamp 30 includes a cylindrical anchor body 40 configured to be telescopically received in hollow throughbore 36. Anchor body 40 includes a transverse bore 42 therethrough and a threaded boss 44 formed coaxially on anchor body 40. A nut 46 is designed to threadedly engage threaded boss 44 so that either longitudinal rod 12 or 13 residing through both transverse bores 38 and 42 can be securely engaged by first side arm clamp 30. Specifically, the tightening of nut 46 on threaded boss 44 pulls anchor body 40 upwardly thereby tightly clamping longitudinal rod 12 or 13 between anchor body 40 and clamp body 32. Advantageously, this secure engagement of longitudinal rod 12 or 13 by first side arm clamp 30 is very secure thereby enabling the surgeon (not shown) to securely affix the relationship between longitudinal rod 12 or 13 and first side arm clamp 30 in a firm, nonrotational relationship. Further, the clamping action of first side arm clamp 30 against longitudinal rod 12 or 13 is exerted in a direction parallel to the axis of anchor body 40 while nut 46 is being tightened so that there are absolutely no rotational forces imposed on longitudinal rods 12 or 13 during this clamping action. This feature is distinctly advantageous to the surgeon since it is highly desirable for the surgeon to be able to securely engage first side arm clamp 30 to longitudinal rods 12 or 13 without having to compensate for any type of rotational forces that would otherwise be imposed on longitudinal rods 12 or 13 if one were to otherwise use a clamping mechanism such as a set screw system (not shown) or such other prior art device.

First side arm clamp 30 provides a highly versatile orientation capability for the placement of side arm 34 relative to longitudinal rods 12 or 13. This feature means that the surgeon (not shown) is able to provide a full range of orientation to the placement of a bone screw 50 (FIGS. 1 and 4) relative to longitudinal rods 12 or 13 as will be discussed hereinafter.

Figure 5:
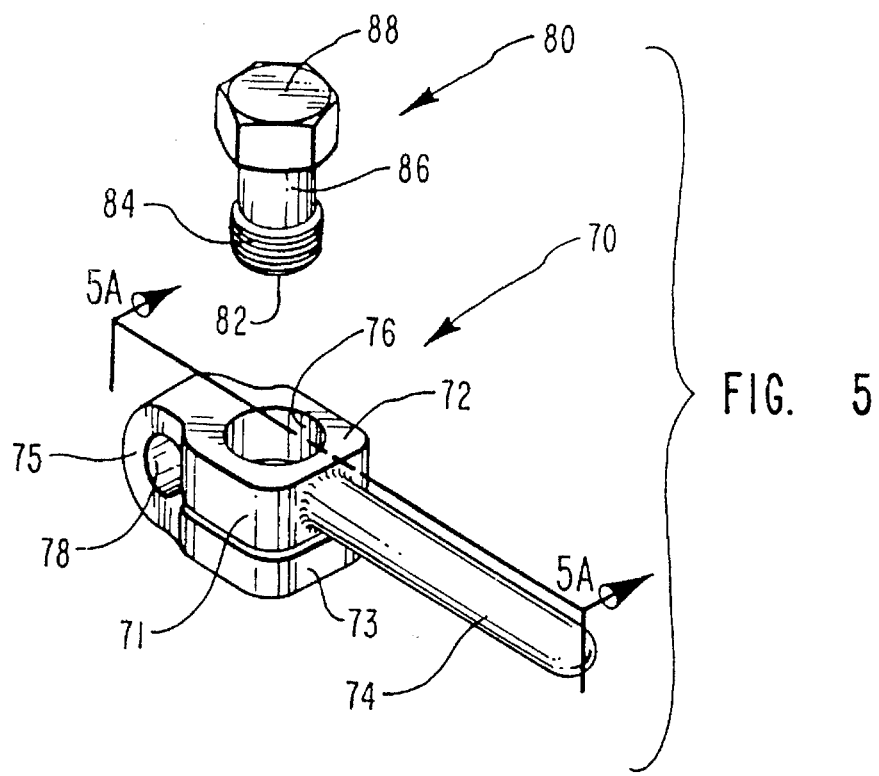
FIG. 5 is an exploded perspective of a second embodiment of a side arm clamp.
Figure 5A:
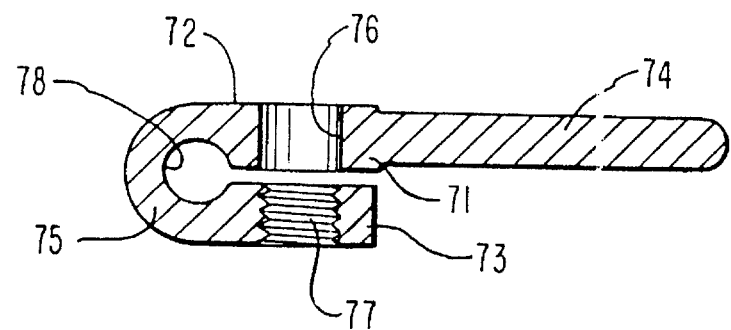
FIG. 5A is a cross sectional view taken along lines 5A—5A of FIG. 5.

Referring now to FIGS. 5 and 5A, a second embodiment of the side arm clamp is shown herein as second side arm clamp 70 having a clamp body 72 configured with a generally C-shaped configuration with an upper jaw 71 and a lower jaw 73. Upper jaw 71 is connected to lower jaw 73 through the sidewall of a hollow, cylindrical sidewall 75 having a throughbore 78 therethrough. Throughbore 78 slidingly receives and ultimately engages longitudinal rods 12 or 13 as will be discussed hereinafter. Importantly, cylindrical sidewall 75 is provided with a limited degree of resiliency upon upper jaw 71 and lower jaw 73 being urged together so that the subject clamping action of longitudinal rods 12 or 13 in throughbore 78 can occur.

Second side arm clamp 70 includes a transverse bore 76 through upper jaw 71 and lower jaw 73 with the portion of transverse bore 76 in lower jaw 73 being threaded with threads 77 (FIG. 5A). Importantly, the diameter of the portion of transverse bore through upper jaw 71 is sufficiently large so that any threaded bolt or screw passed therethrough will pass through freely in a nonbinding relationship while engaging threads 77. Specifically, a bolt 80 is configured with a shaft 82 having a bolt head 88 and a lower threaded portion 84 and a plain shaft 86 extending between lower threaded portion 84 and bolt head 88. Threaded portion 84 is configured to threadedly engage threads 77 to bring bolt head 88 into abutment against upper jaw 71. Further tightening of bolt 80 in second side arm clamp 70 forces the closing together of upper jaw 71 and lower jaw 73. Accordingly, longitudinal rod 12 or 13 residing inside throughbore 78 will be securely engaged by this clamping action.

Figure 4:
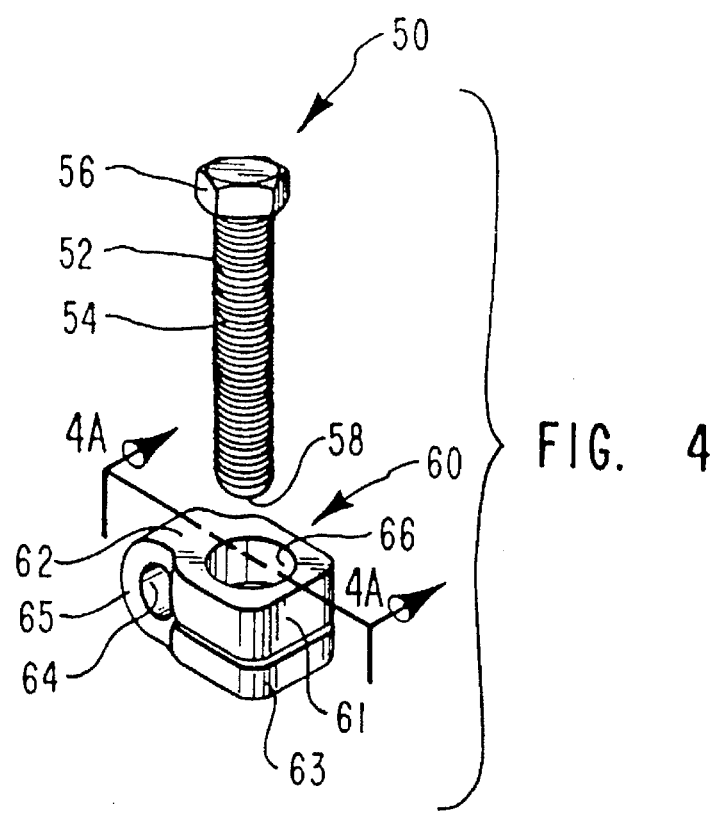
FIG. 4 is an exploded perspective view of a clamp.

While bolt 80 is shown herein as the threaded mechanism for creating the clamping action between upper jaw 71 and lower jaw 73, one of the added features of versatility of this invention is that bone screw 50 (FIGS. 1 and 4) can also be used for this purpose in the event it becomes desirable to secure second side arm clamp through the use of bone screw 50 (FIGS. 1 and 4).

Referring now to FIG. 4, a clamp 60 is shown herein in combination with bone screw 50. Clamp 60 is identical with second side arm clamp 70 (FIGS. 5 and 5A) with the exception that clamp 60 does not include a side arm, side arm 74 (FIGS. 5 and 5A). Clamp 60 includes a clamp body 62 having an upper jaw 61 and a lower jaw 63 interconnected by a cylindrical sidewall 65. A throughbore 64 through clamp body 62 is configured to slidingly receive side arm 34 (FIGS. 3 and 3A) or side arm 74 (FIGS. 5 and 5A) or even longitudinal rods 12 or 13 (FIG. 1). Clamp 60 includes a transverse bore 66, the bottom portion of which in lower jaw 63 is threaded with threads (not shown) identical to threads 77 (FIG. 5A).

Bone screw 50 is configured with a threaded shaft 52 having threads 54 thereon. Bone screw 50 includes a bolt head 56 at its proximal end and terminates in a blunt tip 58 at its distal end. The thread pitch of threads 54 and threads 84 (FIG. 5) is identical to the threads (not shown) in lower jaw 63 as well as threads 77 (FIG. 5A) of second side arm clamp 70 (FIG. 5) thus enabling the surgeon (not shown) to use either bone screw 50 or bolt 80 (FIG. 5) interchangeably in affixing the respective clamp, clamp 60 or second side arm clamp 70 (FIG. 5) as described hereinbefore. The advantage in using bone screw 50 is that it can be used to create a clamping action in either of clamp 60 or second side arm clamp 70 (FIG. 5) while simultaneously securing the respective clamp to spine 90 (FIG. 1).

Referring again to FIG. 1, construct 10 is assembled by mounting first side arm clamps 30a and 30b to longitudinal rods 12 and 13, respectively, after which the various other components of construct 10 are assembled. For example, second side arm clamps 70a–70f are placed in position. Clamps 60a–60h are then affixed to the respective side arms of first side arm clamps 30a and 30b as well as second side arm clamps 70a–70f. Clamps 60a–60h are then securely affixed to the respective sacrum 92 and vertebra 94a–94c using conventional surgical techniques. Specifically, bone screws 50a–50h are used to simultaneously affix the respective clamps 60a–60h to spine 90 and to cause clamps 60a–60h to securely clamp the respective side arm of the respective first or second side arm clamps 30a, 30b, and 70a–70f. First side arm clamps 30a and 30b are then securely clamped to longitudinal rods 12 and 13. Cross-links 20a–20c are mounted between the respective second side arm clamps 70a–70f and second side arm clamps 70a–70f are then tightly clamped to longitudinal rods 12 and 13.

Importantly, construct 10 provides the surgeon (not shown) with a highly versatile spinal fixation apparatus in that the surgeon has the capability to affix bone screws 50a–50h in any preselected angular orientation. Specifically, referring to bone screw 50b, for example, bone screw 50b can be rotated about the axis of the side arm (side arm 74, FIGS. 5 and 5A) of second side arm clamp 70a while, simultaneously, second side arm clamp 70a is rotatable about the axis of longitudinal rod 13. Further, clamp 60b can be moved transversely on the side arm of second side arm clamp 70a while second side arm clamp 70a can be moved longitudinally along longitudinal rod 13. All of these features cause construct 10 to be a highly versatile device for fixation of spine 90. Cross-link plates 20a–20c also provide versatility and rigidity to construct 10 by being adjustably mountable to the respective second side arm clamps 70a–70f which thereby affix the relative position of longitudinal rods 12 and 13. Cross link plates 20a–20c are also configured to be deformably shaped to allow longitudinal rods 12 and 13 to be brought into the desired spatial relationship with spine 90. Construct 10 is configured to be easily conformed to spine 90 versus conforming spine 90 to the prior art devices (not shown) as is open and notoriously known in the art of spine fixation. Increased versatility is also provided by each of the elements of construct 10 being made available in a range of sizes and lengths to accommodate any foreseeable condition expected to be encountered by the surgeon. Further, in the event the surgeon finds (usually through the use of an X-ray) that there is a potential hazard such as a bone screw 50 that is too long such that it protrudes beyond the vertebral body, the surgeon is readily able to remove the offending bone screw 50 and replace it without the necessity of disassembling the rest of construct 10.

Construct 10 is affixed to spine 90 by a very straightforward procedure. Specifically, all of the holes to receive bone screws 50a–50h are sited and then reamed to receive the same. Thereafter, longitudinal rod 12 having the predetermined length and diameter is selected. First side arm clamp 30b is attached to the end thereof and clamp 60h is mounted to its side arm, side arm 34 (FIGS. 3 and 3A). Bone screw 50h is then embedded in sacrum 92 to loosely hold first side arm clamp 30b and longitudinal rod 12 to sacrum 92. During this procedure longitudinal rod 12 is oriented away from spine 90 to protrude upwardly out of the surgical incision (not shown). The surgeon then slips the preselected number of second side arm clamps (second side arm clamps 70d–70f) on longitudinal rod 12. It is important to note that at this point bolt 88 (FIG. 5) is removed from second side arm clamps 70d–70f. Clamp 60e is then affixed to second side arm clamp 70d and clamped thereto by the insertion of bone screw 50e to the pedicle of vertebra 94c. In this manner, longitudinal rod 12 is oriented relative to spine 12. The next step is for the intervening second side arm clamps 70e and 70f to be affixed to spine 90 using clamps 60f and 60g in combination with bone screws 50f and 50g, respectively. Longitudinal rod 13 is then affixed to spine 90 following the identical procedure used for longitudinal rod 12. At this point the surgeon is ready to perform the final alignment of longitudinal rods 12 and 13 by mounting cross-link plates 20a–20c thereto through the mechanism of second side arm clamps 70a–70f, respectively. Specifically, cross-link plates 20a–20c are suitably shaped as described hereinbefore and then mounted between the respective pairs of second side arm clamps 70a–70f by having the bolts therefor (bolt 88, FIG. 5) secured to second side arm clamps 70a–70f. With each of bone screws 50a–50h in place along with first side arm clamps 30a and 30b and second side arm clamps 70a–70f, the surgeon is now ready to make any final adjustment to construct 10 and then suitably tighten all of these elements as needed to achieve the desired fixation of spine 90 with the spinal fixation apparatus of construct 10 without imposing undesirable forces on spine 90.

Specifically, if one has ever attempted to achieve final fixation of two movable elements through the use of a set screw system one has experienced the fact that the act of tightening the set screw almost always results in a rotational movement being imparted by the set screw against the element being engaged by the set screw. To compensate for this characteristic of a set screw, it is customary for the operator to adjust the orientation of the movable element so that when the set screw has been suitably tightened (and rotated the element to, hopefully, its final position) that the element will be at its desired position. Precise final alignment of the two elements using the prior art set screw system is, therefore, a matter of experience coupled with extensive trial and error.

However, with respect to a spinal support system such as construct 10 presented herein, such a final fixation system for the various components of construct 10 is highly impracticable, if not dangerous to the patient. In particular, it is poor medical practice to implant a spinal fixation device in a patient in such a way as to impose unacceptable forces on the spine as a result of the final position setting of the components in the spinal fixation device. Construct 10 eliminates all of these problems by the unique design of its components. For example, the clamping action of first side arm clamp 30 accomplished by the axial pull of anchor body 40. This clamping action imparts absolutely no rotational forces against the particular rod element engaged thereby. Additionally, the clamping action of both second side arm clamp 70 and clamp 60 involve the constriction of the rod element engaged therein, the constriction thereof being accomplished also in the absence of any rotational forces being imposed on the rod element.

Customarily, an X-ray image is taken at some time during the procedure to assure the proper placement and even size of the various elements of construct 10. In the event it is ascertained that one or more of bone screws 50a–50h is of the wrong size, either in length or diameter, they can be easily replaced without disturbing the rest of construct 10. Further, if it is decided that construct 10 should be repositioned in its spatial relationship to spine 90 it can be so repositioned without resort to the disassembly of construct 10. For example, while construct 10 is configured to be mounted quite close to spine 90 it may, in certain circumstances, be desirable to provide an increased spatial separation for the purpose of interposing a greater quantity of bone graft between construct 10 and spine 90.

In summary construct 10 provides a distinct advantage to the surgeon (not shown) in that it allows the surgeon to create any suitable spatial relationship between construct 10 and spine 90 for the purpose of packing bone graft (not shown) therebetween while at the same time providing a very strong, rigid, spinal support system. This advantage is possible through the use of the novel clamping system involved in both first and second side arm clamps 30 and 70 as well as clamp 60. Not only do these clamping devices provide a very solid linkage between components in construct 10 but they also provide a highly advantageous degree of assembly flexibility in assembling construct 10. Specifically, bone screws 50a–50h are almost never secured to spine 90 in a direction that is perpendicular to a plane represented by the axis of longitudinal rods 12 or 13. The ideal placement of bone screws 50a–50h is almost always at some angular offset so that the various components of construct 10 are particularly useful in that they accommodate the precise placement of bone screws 50a–50h regardless of the respective angular orientation. Further, once placed, the entire spinal support apparatus of construct 10 is then securely affixed in the final configuration to thereby provide a rigid spinal support system for spine 90. This latter feature is important and is made possible by the various elements that constitute construct 10.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An implantable device for spinal fixation comprising:

first and second longitudinal rods for placement longitudinally along the spine with said first longitudinal rod on one side of the spinous process and said second longitudinal rod on the other side of the spinous process, said first and second longitudinal rods bridging one or more vertebral segments requiring fixation;

first side arm clamp means selectively mounted to at least one of said first and second longitudinal rods, said first side arm clamp means having a first side arm said first side arm clamp means comprising a plurality of first side arm clamps, each of said first side arm clamps including a clamp body having a cylindrical bore and a cylindrical anchor body in said cylindrical bore, said clamp body including a transverse throughbore through said clamp body and said anchor body, said anchor body including a coaxial threaded boss and a nut threadedly engaged to said threaded boss, a lateral rod extending outwardly from said clamp body in a plane orthogonal to the axis of said transverse throughbore;

clamp means mountable to said first side arm of said first side arm clamp means;

cross link plate means extending between said first longitudinal rod and said second longitudinal rod; and bone screw means for securing said clamp means to the bone of the spine.

2. The implantable device defined in claim 1 wherein said cross link plate means comprises a plurality of cross link plates, each of said cross link plates comprising a planar plate body having a length and a width with a waist formed in said width at a midsection of said length, said planar plate including a slot at each end of said length.

3. The implantable device defined in claim 2 wherein said cross link plate is deformable in a plane orthogonal to the plane of said planar plate to impart a curvature to said cross link plate.

4. An implantable device for spinal fixation comprising:

first and second longitudinal rods for placement longitudinally along the spine with said first longitudinal rod on one side of the spinous process and said second longitudinal rod on the other side of the spinous process, said first and second longitudinal rods bridging one or more vertebral segments requiring fixation;

second side arm clamp means selectively mounted to at least one of said first and second longitudinal rods, said second side arm clamp means having a second side arm, said second side arm clamp means comprises a plurality of second side arm clamps, each of said second side armclamps including a clamp body having a transverse throughbore and a slot extending from said transverse throughbore to the exterior of said clamp body, said slot forming said clamp body into an upper jaw and a lower jaw, said slot forming a spatial separation between said upper jaw and said lower jaw, a bore through said upper jaw and said lower jaw, said bore in said lower jaw including threads, bolt means for passing into said bore and threadedly engaging said threads in said lower jaw to urge said lower jaw toward said upper jaw thereby clamping a rod in said transverse throughbore, a lateral rod extending outwardly from said clamp body in a plane orthogonal to said transverse throughbore, clamp means mountable to said second side arm of said second side arm clamp means;

cross link plate means extending between said first longitudinal rod and said second longitudinal rod; and bone screw means for securing said clamp means to the bone of the spine.

5. The implantable device defined in claim 4 wherein said bolt means comprises said bone screw means.

6. An implantable device for spinal fixation comprising:

first and second longitudinal rods for placement longitudinally along the spine with said first longitudinal rod on one side of the spinous process and said second longitudinal rod on the other side of the spinous process, said first and second longitudinal rods bridging one or more vertebral segments requiring fixation;

first side arm clamp means selectively mounted to at least one of said first and second longitudinal rods, said first side arm clamp means having a first side arm;

second side arm clamp means selectively mounted to at least one of said first and second longitudinal rods, said second side arm clamp means having a second side arm;

clamp means mountable to said first side arm of said first side arm clamp means and to said second side arm of said second side arm clamp means, said clamp means comprising a plurality of clamps, each of said clamps including a clamp body having a transverse throughbore through said clamp body and a slot extending from said transverse throughbore to the exterior of said clamp body, said slot forming said clamp body into an upper jaw and a lower jaw, said slot forming a spatial separation between said upper jaw and said lower jaw, a bore through said upper jaw and said lower jaw, said bore in said lower jaw including threads, said bone screw means threadedly engaging said threads to resiliently urge said lower jaw toward said upper jaw, cross link plate means extending between said first longitudinal rod and said second longitudinal rod; and bone screw means for securing said clamp means to the bone of the spine.

7. An implantable device for spinal fixation comprising:

a first longitudinal rod for placement longitudinally along one side of the spinous process of the spine said first longitudinal rod bridging one or more vertebral segments requiring fixation;

first clamping means engaged to said first longitudinal rod, said first clamping means comprising a first side arm clamp comprising a clamp body having an axial bore and a transverse throughbore, said first side arm clamp including an anchor body telescopically receivable in said axial bore, said anchor body having a transverse bore operable to be placed in alignment with said transverse throughbore to receive a rod therethrough, said anchor body including a threaded boss extending coaxially from said anchor body, a nut threadedly engaged to said threaded boss for moving said anchor body incrementally relative to said clamp body to thereby securely engage said rod in said transverse throughbore and said transverse bore, said clamp body including a side arm extending outwardly from said clamp body orthogonally to the axis of said transverse throughbore;

first plurality of second clamping means each configured to engage said first lateral rod; and first plurality of bone screw means for engaging the bone of the spine, each of said bone screw means operable to engage said second clamping means to said lateral rod.

8. The implantable device for spinal fixation defined in claim 7 comprising a second longitudinal rod for placement longitudinally along the other side of the spinous process of the spine and generally parallel to said first longitudinal rod, said second longitudinal rod including a second plurality of said first clamping means with a second plurality of said second clamping means engaged to said first lateral rod and a second plurality of said bone screw means for engaging the bone of the spine while causing said second clamping means to engage said lateral rod of said second plurality of first clamping means; and a plurality of cross link plates extending laterally between said first longitudinal rod and said second longitudinal rod, each of said cross link plates having a first end and a second end, said first end having a first hole for use in securing said first end to a first clamping means of said first plurality, said second end having a second hole for use in securing said second end to a first clamping means of said second plurality.

9. The implantable device for spinal fixation defined in claim 8 wherein said cross link plate comprises a planar plate having a length, a width and a waist in said width midway along said length, said waist providing said cross link plate with selective deformability, said cross link plate including an elongated slot at each end of said length.

10. The implantable device for spinal fixation defined in claim 9 wherein said cross link plate includes bolt means for bolting said cross link plate to said first clamping means and said second clamping means.

11. An implantable device for spinal fixation comprising:

a first longitudinal rod for placement longitudinally along one side of the spinous process of the spine said first longitudinal rod bridging one or more vertebral segments requiring fixation;

first clamping means engaged to said first longitudinal rod;

a first plurality of second clamping means each configured to engage said first lateral rod, said second clamping means comprises a second side arm clamp comprising a clamp body having a transverse throughbore and a slot in said clamp body, said slot extending between said transverse throughbore and the exterior of said clamp body thereby forming said clamp body into an upper jaw and a lower jaw with said clamp body having sufficient resiliency adjacent said transverse throughbore opposite said slot to accommodate said lower jaw being urged toward said upper jaw, said clamp body having a bore through said upper jaw and said lower jaw, said bore in said lower jaw including threads for threadedly receiving a bolt means inserted into said bore, bolt means for threadedly engaging said threads and tightening said lower jaw toward said upper jaw thereby constricting a rod engaged in said transverse throughbore, said clamp body including a side arm extending outwardly from said clamp body orthogonally to the axis of the bore; and a first plurality of bone screw means for engaging the bone of the spine, each of said bone screw means operable to engage said second clamping means to said lateral rod.

12. A method for providing fixation to a spine with an implantable device comprising the steps of:

selecting two longitudinal rods, each of said longitudinal rods having a length sufficient to span the portion of the spine requiring fixation;

orienting said longitudinal rods on each side of the spinous process of the spine;

mounting a plurality of side arm clamping means to each longitudinal rod, each side arm clamping means including a lateral arm extending outwardly from said longitudinal rod to which said side arm clamping means is mounted, said mounting step including mounting said side arm clamping means which comprise a first side arm clamp having a cylindrical body with a coaxial bore through said cylindrical body and cylindrical anchor body inserted in said coaxial bore, said cylindrical body and said cylindrical anchor body having a transverse throughbore for receiving said longitudinal rods, said cylindrical anchor body having a coaxial threaded boss and a nut threadedly engaged thereto for clamping said longitudinal rod in said transverse throughbore;

placing a clamp on each lateral arm of said side arm clamping means;

securing each of said clamp to said lateral arm and to a bone of the spine with a bone screw; and attaching a plurality of cross link plates between said side arm clamping means on said first longitudinal rod and said side arm clamping means on said second longitudinal rod.

13. The method defined in claim 12 wherein said attaching step includes deformably shaping said cross link plates thereby conforming said implantable device to the spine.

14. The method defined in claim 12 wherein said placing step includes rotating said clamp relative to said lateral arm and said side arm clamping means relative to said longitudinal rod thereby providing optimal angular orientation of said bone screw to the spine.

15. The method defined in claim 12 wherein said method includes adjustably orienting the spatial relationship of said implantable device relative to the spine by selectively deforming said cross link plates and positioning said plurality of side arm clamps relative to said longitudinal rods and said clamps on said lateral arms.

16. A method for providing fixation to a spine with an implantable device comprising the steps of:

selecting two longitudinal rods, each of said longitudinal rods having a length sufficient to span the portion of the spine requiring fixation;

orienting said longitudinal rods on each side of the spinous process of the spine;

mounting a plurality of side arm clamping means to each longitudinal rod, each side arm clamping means including a lateral arm extending outwardly from said longitudinal rod to which said side arm clamping means is mounted, said mounting step including mounting said side arm clamping means which comprise a second side arm clamping means having a pair of jaws operable for constricting a transverse throughbore adjacent said jaws, said jaws including an upper jaw and a lower jaw and a bore through said upper jaw and said lower jaw, said bore in said lower jaw including threads for threadedly receiving a bolt for constricting a longitudinal rod in said transverse throughbore;

placing a clamp on each lateral arm of said side arm clamping means;

securing each of said clamp to said lateral arm and to a bone of the spine with a bone screw; and attaching a plurality of cross link plates between said side arm clamping means on said first longitudinal rod and said side arm clamping means on said second longitudinal rod.

17. The method defined in claim 16 wherein said attaching step includes deformably shaping said cross link plates thereby conforming said implantable device to the spine.

18. The method defined in claim 16 wherein said placing step includes rotating said clamp relative to said lateral arm and said side arm clamping means relative to said longitudinal rod thereby providing optimal angular orientation of said bone screw to the spine.

19. The method defined in claim 16 wherein said method includes adjustably orienting the spatial relationship of said implantable device relative to the spine by selectively deforming said cross link plates and positioning said plurality of side arm clamps relative to said longitudinal rods and said clamps on said lateral arms.

* * * * *